(12) United States Patent
Kanie et al.

(10) Patent No.: US 6,664,235 B1
(45) Date of Patent: Dec. 16, 2003

(54) MEDICAMENTS COMPRISING SIALIC ACID DERIVATIVES AS ACTIVE INGREDIENTS

(75) Inventors: Osamu Kanie, Saitama (JP); Chi-Huey Wong, Saitama (JP); Yasuo Suzuki, Shizuoka (JP)

(73) Assignee: Riken, Saitama (JP)

( * ) Notice: Subject to any disclaimer, the term of this patent is extended or adjusted under 35 U.S.C. 154(b) by 345 days.

(21) Appl. No.: 09/640,776

(22) Filed: Aug. 18, 2000

(30) Foreign Application Priority Data

Aug. 20, 1999 (JP) .......................................... 11-234224

(51) Int. Cl.⁷ ..................... A61K 31/7028; C07H 15/02
(52) U.S. Cl. ..................... 514/25; 536/17.2; 536/17.9; 536/18.2; 536/18.3; 536/18.4
(58) Field of Search ............... 536/17.2, 17.9, 536/18.2–18.4; 514/25

(56) References Cited

U.S. PATENT DOCUMENTS

| | | | | |
|---|---|---|---|---|
| 4,151,268 A | * | 4/1979 | Spector | 424/1 |
| 5,077,397 A | * | 12/1991 | Yoshimura et al. | 536/53 |
| 5,192,661 A | * | 3/1993 | Roy et al. | 435/7.23 |
| 5,639,786 A | | 6/1997 | Von Itzstein et al. | 514/459 |
| 5,648,379 A | | 7/1997 | Von Itzstein et al. | 514/459 |

FOREIGN PATENT DOCUMENTS

| JP | 10-182686 | * | 7/1998 |
|---|---|---|---|
| JP | 11147951 | | 6/1999 |
| JP | 11343295 | | 12/1999 |

OTHER PUBLICATIONS

Bianco, A. et al "Neuraminic acid derivatives as anti–influenza drugs" Molecules Online, vol 2, pp. 129–136, 1998.*
English Language Abstract of JP 11–147951, 1999.
English Language Abstract of JP 11–343295, 1999.
Von Itzstein, M., et al., Nature, vol. 363, 418–423 (1993).
Suzuki, Y., et al., Virology, vol. 189, 121–131 (1992).
Sun, X–L., et al., Eur. J. Org. Chem. 2643–2653 (2000).
Guo, C–T., et al., Glycoconjugate Journal, vol. 15, 1099–1108 (1998).
Food and Drug Administration Talk Paper, FDA Approves Relenza (Zanamivir for Inhalation) for Influenza Treatment, Jul. 27, 1999.
Okamoto, K., et al., Bull. Cham. Soc. Japan, vol. 60, 631–636 (1987).

* cited by examiner

*Primary Examiner*—Kathleen K. Ponda
*Assistant Examiner*—Leigh C. Maier
(74) *Attorney, Agent, or Firm*—Greenblum & Bernstein, P.L.C.

(57) ABSTRACT

A medicament for treatment of a viral infection which comprises as an active ingredient a compound represented by the following formula (I) or its Pharmaceutically acceptable salt, or a hydrate thereof or a solvate thereof.

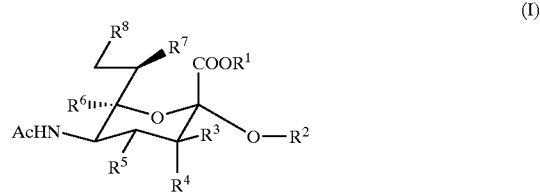

(I)

wherein $R^1$ represents hydrogen atom or a $C_{1-6}$ alkyl group; $R^2$ represents an optionally substituted phenyl group, a $C_{1-20}$ alkyl group, a $C_{1-20}$ alkenyl group, or—$(CH_2)_k$—[NH—$(CH_2)_m$—NH]$_n$—Y or —$(CH_2)_k$—[NH—$(CH_2CH_2O)_{m-1}$—$CH_2CH_2NH]_n$—Y in which Y represents phosphatidylethanolamine residue or polyglutamic acid residue, k and m independently represent an integer of from 2 to 10, n represents 0 or 1, provided that when n represents 1, Y represents phosphatidylethyl group; $R^3$ represents hydrogen atom or an optionally substituted hydroxyl group; $R^4$ represents hydrogen atom, a halogen atom, azide group, an optionally substituted amino group, or an optionally substituted hydroxyl group; and $R^5$, $R^6$, $R^7$ and $R^8$ independently represent an optionally substituted hydroxyl group.

18 Claims, No Drawings

MEDICAMENTS COMPRISING SIALIC ACID DERIVATIVES AS ACTIVE INGREDIENTS

TECHNICAL FIELD

The present invention relates to medicaments comprising a sialic acid derivative as an active ingredient.

BACKGROUND ART

Viruses including influenza virus proliferate depending on the biosynthesis mechanism of the host. Therefore, it is difficult to develop medicaments which can exert sufficient antiviral action specifically on viruses, and only a few medicaments which can exert clinically high effectiveness are known. For the treatment of viral infections, vaccines have been used as the most effective means so far. However, there are problems that vaccines cannot be prepared and used when a causal virus is not identified, and that effectiveness of a prepared vaccine can hardly be expected against a virus with rapid variation.

There are types A, B and C of influenza viruses, and the virus type A is known to drastically change the structure of the antigen protein and pass through the immune mechanism of a human as a host, so that a problem arises that vaccine treatment fails to achieve sufficient effectiveness.

Influenza viruses have two spike glycoproteins, trimer hemagglutinin (HA) and tetramer sialidase (NA). They form infection through polyvalent specific action of the hemagglutinin (HA) and the sialoglycoside chain receptor of host cells. The viruses, after proliferation by destruction of the virus receptor by sialidase (NA), are released from the host cells. These two proteins recognize the sialoglycoside chain as ligands which exist on the surface of the host cell. Accordingly, it can be considered that the infection of influenza viruses can be inhibited by interference of the interaction of these two proteins and the sialoglycoside chain.

Recently, a highly effective antiviral agent has been developed on the basis of analysis of the crystal structure of sialidase which is one of the two viral membrane proteins of influenza viruses (von Itzstein, M. et al., Nature, 363, 1993). However, this antiviral agent cannot inhibit the formation of infection, per se, since sialidase does not participate in the first stage of the infection. Therefore, it is necessary to develop antiviral agents which can exert potent inhibitory action against both of the two membrane proteins, i.e., sialidase and hemagglutinin.

It has been reported so far that a sialyl-lactose-containing polymer has potent inhibitory activity against type H1 virus HA (Japanese Patent Unexamined Publication (KOKAI) (Hei) No.11-147951/1999), and a polymer binding to sialic acid monosaccharide to form C- or S-glycoside has potent inhibitory action on type H3 virus HA.

However, no compound has been reported so far which is a sialic acid derivative having a low molecular weight and can exert potent inhibitory action against the two membrane proteins (sialidase and hemagglutinin).

The inventors of the present invention succeeded in synthesizing sialic acid derivatives having a substituent on the carbon atom in the 3-position on the basis of studies conducted so far to provide a compound which can be expected to exert excellent antiviral activity on viruses including influenza viruses (Japanese Patent Unexamined Publication (KOKAI) No.(Hei)11-343295/1999; The 20th Carbohydrate Symposium, July 1998). However, these sialic acid derivatives have not been verified to have antiviral activity on influenza viruses.

DISCLOSURE OF THE INVENTION

An object of the present invention is to provide novel medicaments comprising a sialic acid derivative, especially a sialic acid derivative having a low molecular weight. More specifically, the object is to provide medicaments for preventive and/or therapeutic treatment of viral diseases such as influenza virus infectious diseases.

Another object of the present invention is to provide novel medicaments comprising a sialic acid derivative having resistance against hydrolysis by sialidase, more specifically, medicaments for preventive and/or therapeutic treatment of viral diseases such as influenza virus infectious diseases.

The inventors of the present invention conducted intensive studies to solve the aforementioned problems. As a result, they found that sialic acid derivatives which may be substituted on the carbon atom in the 3-position have resistance to hydrolysis and inhibitory action against the membrane binding proteins of influenza viruses, and another membrane enzyme sialidase. The present invention was achieved on the basis of these finding.

The present invention thus provides medicaments which comprise as an active ingredient a compound represented by the following formula (I) or its pharmaceutically acceptable salt, or a hydrate thereof or a solvate thereof

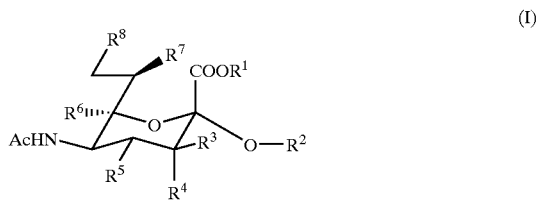

wherein $R^1$ represents hydrogen atom or a $C_{1-6}$ alkyl group; $R_2$ represents an optionally substituted phenyl group, a $C_{1-20}$ alkyl group, a $C_{1-20}$ alkenyl group, or $-(CH_2)_k-[NH-(CH_2)_m-NH]_n-Y$ or $-(CH_2)_k-[NH-(CH_2CH_2O)_{m-1}-CH_2CH_2NH]_n-Y$ in which Y represents phosphatidylethanolamine residue or polyglutamic acid residue, k and m independently represent an integer of from 2 to 10, n represents 0 or 1, provided that when n represents 1, Y represents phosphatidylethyl group; $R^3$ represents hydrogen atom or an optionally substituted hydroxyl group; $R^4$ represents hydrogen atom, a halogen atom, azide group, an optionally substituted amino group, or an optionally substituted hydroxyl group; and $R^5$, $R^6$, $R^7$ and $R^8$ independently represent an optionally substituted hydroxyl group.

Preferably, the medicaments of the present invention are those for preventive and/or therapeutic treatment of viral diseases.

More preferably, the medicaments of the present invention are those for preventive and/or therapeutic treatment of influenza virus infectious diseases.

More specifically, the medicaments of the present invention have inhibitory action against infection and/or proliferation of influenza viruses.

Preferably, in the formula (I), $R^2$ represents $-(CH_2)_k-[NH-(CH_2)_m-NH]_n-Y$ or $-(CH_2)_k-[NH-(CH_2CH_2O)_{m-1}-CH_2CH_2NH]_n-Y$ in which Y represents phosphatidylethanolamine residue or polyglutamic acid residue, k and m independently represent an integer of from 2 to 10, n represents 0 or 1, provided that when n represents 1, Y represents phosphatidylethyl group.

Further preferably, in the formula (I), $R^2$ represents —$(CH_2)_k$—Y wherein Y represents phosphatidylethanolamine residue, and k represents an integer of from 2 to 10.

Preferably, one of $R^3$ and $R^4$ is hydrogen atom, and the other is a halogen atom or an optionally substituted hydroxyl group.

Further preferably, $R^3$ is hydrogen atom, and $R^4$ is a halogen atom or an optionally substituted hydroxyl group.

Preferably, $R^1$ is hydrogen atom.

From another aspect of the present invention, there are provided use of a compound represented by the above formula (I) or a pharmaceutically acceptable salt thereof, or a hydrate thereof or a solvate thereof for the manufacture of a medicament, in particular, a medicament for preventive and/or therapeutic treatment of viral infectious disease such as influenza viral infections; and a method for preventive and/or therapeutic treatment of viral infectious diseases such as influenza viral infections which comprises the step of administering to a mammal including human an effective amount of a compound represented by the above formula (I) or a pharmaceutically acceptable salt thereof, or a hydrate thereof or a solvate thereof.

BEST MODE FOR CARRYING OUT THE INVENTION

The meanings of the terms used herein are as follows. The alkyl group or an alkyl moiety of a functional groups containing the alkyl moiety may be linear, branched, or cyclic alkyl groups, or a combination thereof. Examples include methyl group, ethyl group, n-propyl group, isopropyl group, cyclopropyl group, n-butyl group, sec-butyl group, tert-butyl group, cyclopropylmethyl group, and cyclobutyl group.

When the phenyl group represented by $R^2$ is substituted, the number of the substituent and the substituting position are not particularly limited. Examples include substituted or unsubstituted $C_{1-6}$ alkyl groups such as methyl group, trifluoromethyl group, and hydroxyethyl group; $C_{1-6}$ alkoxyl groups such as methoxy group and ethoxy group; halogen atoms (a halogen atom used herein may be any of fluorine, chlorine, bromine and iodine atoms); substituted or unsubstituted $C_{1-6}$ alkanoyl groups such as acetyl group and trifluoroacetyl group; substituted or unsubstituted aralkyl groups such as benzyl group, p-methoxybenzyl group and p-chlorobenzyl group; nitro group; cyano group; substituted or unsubstituted aryl groups such as phenyl group and chlorophenyl group; substituted or unsubstituted aroyl groups such as benzoyl group and chlorobenzoyl group; carboxyl group; $C_{1-6}$ alkoxycarbonyl groups such as ethoxycarbonyl group and tert-butoxycarbonyl group; and substituted or unsubstituted amino groups such as amino group, monomethylamino group and acetylamino group. However, the substituents are not limited to these examples. Among them, nitro group is preferred, and substitution in the p-position is preferred.

The $C_{1-20}$ alkyl group or the $C_{1-20}$ alkenyl group represented by $R^2$ may be linear, branched, or cyclic, or a combination thereof. The number of unsaturated bonds in the alkenyl group is not particularly limited, for example from 1 to 3, and preferably 1.

In the group represented by —$(CH_2)_k$—[NH—$(CH_2)_m$—NH]$_n$—Y or —$(CH_2)_k$—[NH—$(CH_2CH_2O)_{m-1}$—$CH_2CH_2NH]_n$—Y, Y represents phosphatidylethanolamine residue or polyglutamic acid residue, and preferably, k is 2 and n is 0. In these groups, the nitrogen atom of the phosphatidylethanolamine in Y preferably binds to —$(CH_2)_k$—. N-terminal acetylated polyglutamic acid residue is preferably used as the polyglutamic acid residue, and preferably k is 2 and n is 1.

In the present invention, $R^2$ preferably represents —$(CH_2)_k$—[NH—$(CH_2)_m$—NH]$_n$—Y or —$(CH_2)_k$—[NH—$(CH_2CH_2O)_{m-1}$—$CH_2CH_2NH]_n$—Y, most preferably —$(CH_2)_k$—[NH—$(CH_2)_m$—NH]$_n$—Y, wherein Y represents phosphatidylethanolamine residue or polyglutamic acid residue, k and m independently represent an integer of from 2 to 10, n represents 0 or 1, provided that when n represents 1, Y represents phosphatidylethyl group Most preferably, $R^2$ represents —$(CH_2)_k$—Y wherein Y represents phosphatidylethanolamine residue, and k represents an integer of from 2 to 10.

When $R^3$, $R^4$, $R^5$, $R^6$, $R^7$ or $R^8$ represents a substituted hydroxyl group, the substituent of the hydroxyl group is not particularly limited, and examples include substituents commonly used as protective groups for hydroxyl group and those used for eliminating hydroxyl group. Examples include, for example, substituted or unsubstituted $C_{1-6}$ alkanoyl groups such as acetyl group and trifluoroacetyl group; substituted or unsubstituted aralkyl groups such as benzyl group, p-methoxybenzyl group and p-chlorobenzyl group; alkylsilyl groups such as trimethylsilyl group; substituted or unsubstituted $C_{1-6}$ alkyl groups such as methyl group, trifluoromethyl group and hydroxyethyl group; substituted or unsubstituted aryl groups such as phenyl group and chlorophenyl group; substituted or unsubstituted aroyl groups such as benzoyl group and chlorobenzoyl group; $C_{1-6}$ alkoxycarbonyl groups such as ethoxycarbonyl group and tert-butoxycarbonyl group; and substituted sulfonyl groups such as p-toluenesulfonyl group, methanesulfonyl group and trifluorometbanesulfonyl group. However, substituents are not limited to these examples.

When $R^4$ represents a substituted amino group, one or more substituents on the amino group may be the same or different, and types of the substituent are not particularly limited. For example, those commonly used as amino-protective groups are suitably used. Such substituents include, for example, substituted or unsubstituted $C_{1-6}$ alkanoyl groups such as acetyl group and trifluoroacetyl group; substituted or unsubstituted aralkyl groups such as benzyl group, p-methoxybenzyl group and p-chlorobenzyl group; substituted or unsubstituted $C_{1-6}$ alkyl groups such as methyl group, trifluoromethyl group and hydroxyethyl group; substituted or unsubstituted aryl groups such as phenyl group and chlorophenyl group; substituted or unsubstituted aroyl groups such as benzoyl group and chlorobenzoyl group; and $C_{1-6}$ alkoxycarbonyl groups such as ethoxycarbonyl group and tert-butoxycarbonyl group. However, substituents are not limited to these examples.

The compound represented by the aforementioned formula (I) may sometimes form a salt according to the type of the gubstituent. As the medicament of the present invention, pharmaceutically acceptable salts of the compound represented by the aforementioned formula (I) may be used. Examples of the salt include mineral acid salts such as hydrochloride and sulfate; or organic acid salts such as p-toluenesulfonate; metal salts such as sodium salt, potassium salt and calcium salt; ammonium salt; organic ammonium salts such as methylammonium salt; and amino acid salts such as glycine salt. In addition to the compounds in free form or their salts, any hydrates thereof or solvates thereof may also be used.

The compounds represented by the aforementioned formula (I) have asymmetric carbon atoms and they may exist as optically active compounds. Any stereoisomers such as optical isomers or diastereoisomers, any mixtures of such stereoisomers, racemates and the like can be used in the present invention. As for the expression of stereochemistry of $R^6$ and $R^7$ in the aforementioned formula (I), their relative configurations are shown. However, it should not be interpreted that the formula shows absolute configuration of the compound represented by the aforementioned formula (I).

Among the compounds of the present invention, those wherein $R^2$ is an optionally substituted phenyl group can be prepared, for example, from a known bromohydrin compound (Okamoto, K., et al., Bull. Chem. Soc. Jpn., 60, pp.631–636, 1987) according to the method shown in the following scheme. In the scheme, Ac represents acetyl group; Me represents m ethyl group; Tf represents trifluoromethanesulfonyl group; Py represents pyridine; DMF represents dimethylformamide; THF represents tetrahydrofuran; and TASF represents tris(dimethylamino)sulfonium difluoromethylsilicate.

limited, and those prepared by any methods can be used in the present invention.

The compounds wherein $R^2$ is a $C_{1-20}$ alkyl group or a $C_{1-20}$ alkenyl group can be prepared by introducing an alkyl group or an alkenyl group to an epoxy compound described in Bull. Chem. Soc. Jpn., 60, pp.637–643, Okamoto, K., et al., 1987, and eliminating a protective group, if necessary.

The compounds having —$(CH_2)_k$—Y wherein Y is phosphatidylethanolamine residue can be prepared by ozonolysis of a compound introduced with an alkenyl group such as allyl group, and reacting the resulting ketone or aldehyde compound with phosphatidylethanolamine. The compounds introduced with polyglutamic acid residue can be prepared by reacting the above ketone compound with a diamine compound represented by $H_2N$—$(CH_2)_m$—$NH_2$ or $H_2N$—$(CH_2CH_2O)_{m-1}$—$CH_2CH_2NH_2$ as a linker, and further reacting the amino group at the terminal of the reaction product with a reactive acetylated polyglutamic acid derivative. As method for introducing polyglutamic acid, for

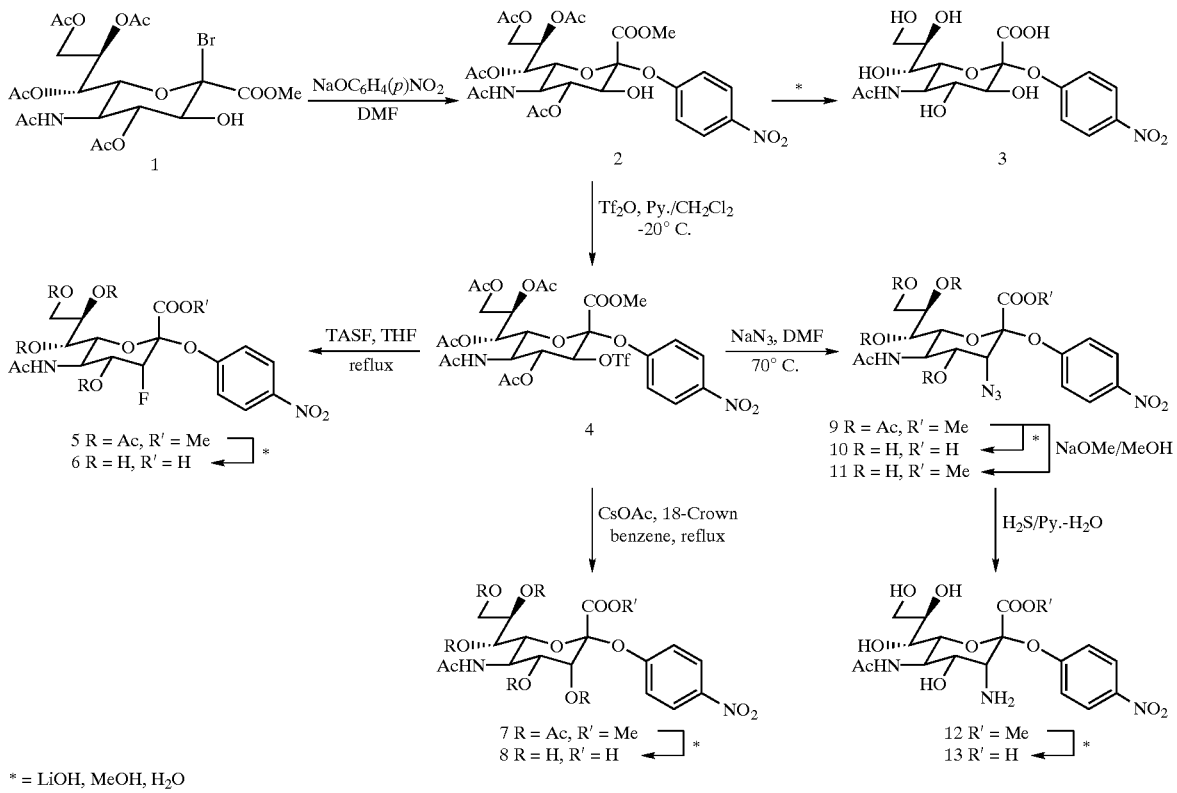

* = LiOH, MeOH, $H_2O$

Specific and detailed explanations of preparation of the typical compounds shown in the above scheme are given in examples of Japanese Patent Unexamined Publication (KOKAI) No. (Hei)11-343295/1999. Accordingly, any compound falling within the aforementioned formula (I) can be easily prepared by appropriately choosing starting materials, reagents, conditions and the like according to the method described therein, and applying appropriate modifications and alterations, if necessary The descriptions of Japanese Patent Unexamined Publication (KOKAI) No.(Hei)11-343295/1999 are incorporated herein as disclosures by reference.

However, methods for preparing the compounds used according to the present invention are not particularly example, the method descried in Japanese Patent Unexamined Publication (KOKAI) (Hei) No.11-147951/1999 can be applied.

The compounds represented by the aforementioned formula (I) or their pharmaceutically acceptable salts, or hydrates thereof and solvates thereof used in the present invention have inhibitory activities against both of hemagglutinin and sialidase which are membrane binding proteins of influenza virus. They are also expected to have similar inhibitory activities on membrane binding proteins of other viruses. Some of the compounds represented by the aforementioned formula (I) or their pharmaceutically acceptable salts, or hydrates thereof and solvates thereof used in the present invention have resistance to sialidase hydrolysis.

Accordingly, their administrations may be effective treatment of diseases in which sialic acid recognition occurs in an initial stage of infection.

Therefore, the compounds represented by the aforementioned formula (I) or their pharmaceutically acceptable salts, or hydrate thereof or solvate thereof are useful as active ingredients of medicaments for preventive and/or therapeutic treatment of viral diseases such as influenza viral infections.

Examples of diseases to be applied by the medicaments of the present invention include, for example, to influenza, viral hepatitis (types A, B, C, E, or the like), viral pneumonia, viral bronchitis, herpesvirus infectious diseases, polio, AIDS, adult T cell leukemia, papiroma, measles, rubella, sudden eruption, infectious erythema, viral encephalitis, viral meningitis, cytomegalovirus infectious diseases, epidemic parotitis, varicella, rabies, and viral enteritis, and a preferred example includes influenza.

As the active ingredient of the medicament provided by the present invention, a substance can be used which is selected from the group consisting of the compounds as free form represented by the aforementioned formula (I) and their salts, and hydrates thereof and solvates thereof.

In general, the medicament of the present invention is provided in a form of a pharmaceutical composition which comprises the aforementioned active ingredient and one or more pharmaceutical additives such as carriers and excipients.

The administration route of the medicament of the present invention is not particularly limited, and oral administration or parenteral administration such as intramuscular, intravenous, subcutaneous and intraperitoneal administration, transmucosal administration to nasal fossa and the like, and inhalation may be applied.

The form of the medicament of the present invention is not particularly limited. Examples of formulations for oral administration include, for example, tablets, capsules, fine granules, granules, liquids and syrups, and examples of formulations for parenteral administration include, for example, injections, drip infusions, suppositories, inhalants, transmucosal preparation, transdermal preparations, nasal drops, and ear drops.

The forms of the medicamnents of the present invention, pharmaceutical additives to be used, methods of preparation of formulations and the like can be appropriately chosen by one of ordinary skill in the art.

Dose of the medicament of the present invention can be appropriately chosen by comprehensive consideration of sexuality, age or body weight of a patient, severity of a disease, a purpose of preventive and/or therapeutic treatment, presence or absence of other complication and the like. In general, the dose may be 0.001 to 1,000 μg/kg of body weight per day, preferably 0.001 to 100 μg/kg of body weight per day.

EXAMPLES

The present invention will be explained more specifically with reference to the following examples. However, the scope of the present invention is not limited to these examples.

Test Compounds

The following sialic acid derivatives 1 to 10 were used in experiments. Preparations of these compounds are described in Japanese Patent Unexamined Publication (KOKAI) No. (Hei)11-343295/1999 and the like.

|   | X | $R^1$ | $R^2$ |
|---|---|---|---|
| 1 | O-4-MU | H | H |
| 2 | O-4-PNP | H | H |
| 3 | O-4-PNP | OH | H |
| 4 | O-4-PNP | H | OH |
| 5 | O-4-PNP | H | F |
| 6 | O-DSPE | H | H |
| 7 | O-DSPE | OH | H |
| 8 | O-DSPE | H | OH |
| 9 | O-DSPE | H | F |

10

Test Example 1

Resistance to Sialidase Hydrolysis and Sialidase Inhibitory Activity of the Sialic Acid Derivatives The p-nitrophenyl-α-O-glycoside optionally having a substituent in the 3-position (Compounds 2 to 5 and 10) were used as test compounds to examine (1) resistance to acid hydrolysis, (2) resistance to enzymatic (sialidase) hydrolysis, (3) sialidase inhibitory activity (kinetic analysis), (4) inhibitory activity against hemagglutinin, and (5) inhibition of infection of influenza virus to MDCK cells.

(1) Test of Resistance to Acid Hydrolysis

In thee test of resistance to acid hydrolysis, 4 to 10 MM of Compounds 2 to 5 and 24 (in 0.6 mL of 1.0 N $D_2SO_4/D_2O$ (pD 1.37) were used. Hydrolysis was observed with time by $^1$H NMR (270 $MH_2$) at 50° C. using a spectrometer JEOL EX-270. The spectral data was collected at 3-hour intervals with 2 seconds of acquisition time and 20 scan untill hydrolysis progressed to 50%. Reaction yields were calculated from relative integration of signals corresponding to aromatic protons (H-3',5' and H-2',6') of the substrates to those of p-nitrophenol.

(2) Test of Resistance to Enzymatic Hydrolysis (Hydrolysis Catalyzed by Sialidasc)

50 mM acetic buffer (pH 5.5 for sialidase from Arthrobacter Ureafaciens; pH 5.0 for sialidase from Clostridium perfringens; and pH 5.5 for sialidase from Vibrio cholcrae), 0.5 mM p-nitrophenyl-α-O-glycoside of sialic acid, a test compound (Compounds 2 to 5 and 24), and sialidase (20 mU Arthrobacter Ureafaciens sialidase; 15 mU Clostridium perfringens sialidase; and 50 mU Vibrio cholerae sialidasc: all were purchased from Bochringer Mannheim Gmbh) were mixed. The mixture was maintained at 37° C. and a part of the reaction mixture (about 10 μL) was continually sampled. The reaction was stopped with 200 mM aqueous $Na_2CO_3$ of 10 μL, and capillary electrophoresis was carried out as follows.

The measurement was made by using a Water Quanta 4000E capillary electrophoresis apparatus. As a capillary column, a fused silica capillary column (inside diameter of 75 μm, effective length of 53 cm) was used. The capillary column was washed with 0.1 M KOH for 2 minutes before introducing the sample, and substituted with a electrophoresis buffer. Injection of the sample was made by the siphon effect at the height difference of 10 cm for 30 seconds (38.4 nL). Electrophoresis was carried out by using 50 mM boric buffer (pH 10.2) as an electrolyte at voltage of 20 kV and at a constant temperature of 37° C. Detection was made at 7.6 cm from the anode by ultraviolet absorption (405 nm). Results were analyzed by using Millienium 2010 system (Millipore).

(3) Sialidase Inhibitory Activity (Kinetic Analysis).

$IC_{50}$ of the test compounds (Compounds 2 to 5 and 10) was determined, and then, using the buffer used in the aforementioned hydrolysis test, the reaction mixture was added with 4-methylumbelliferyl-α-D-N-acetylneuraminic acid (Compound 1) (0.4 mM) as a substrate, a compound verified to have an inhibitory action, and sialidase (1.25 mU Arthrobacter Ureafaciens; 0.1 mU Clostridium perfringens sialidase; and 2.0 mU Vibrio cholerae sialidase) to adjust a final volume of 30 μL, and maintained at 37° C. for 10 minutes. The reaction was stopped with 30 μL of 200 mM $Na_2CO_3$ and measurement was carried out using capillary electrophoresis as follows.

Please replace the second paragraph at page 15 with the following paragraph (clean text; a marked-up copy of the replacement paragraph is attached as an Appendix hereto):

In the measurement, a Backman P/ACE 5010 capillary electrophoresis apparatus and a fused silica capillary column were used. Detection was made by using a He—Cd Laser (Kimmon Electro Co., Ltd., Japan) and excitation light at 325 nm and fluorescence of 375 nm at the point of 7.0 cm from the anode. The sample was injected by the pressurization method (1.0 Sec., 300 nL). Electrophoresis was performed by using 50 mM boric buffer (pH 10.2) as an electrolyte at the applied voltage of 15 kV at 35° C.

The Ki value was estimated from calculation using the following formula on the basis of the $IC_{50}(\%)$ value and the assumption that the inhibition was antagonistic. The $IC_{50}$ value was obtained by using the concentration of the inhibitory substance as a variable.

$$Ki=(i\%\div 100[I])\div(1+[S]\div Km)$$

In the formula, "i" represents inhibitory rate (50%); [I] represents a concentration of an inhibitor; [S] represents a substrate concentration; and Km represents the Michaelis constant.

The results obtained from the three tests are shown in Table 1.

TABLE 1

Stability to acid hydrolysis and enzyme-catalyzing hydrolysis, and neuraminidase inhibition

| Compound | Hydrolysis T½ (hour) 1N sulfuric acid 50° C. | Hydrolysis (%) NAs* 24 hours | Ki (M) NA (C. perfringens**) |
|---|---|---|---|
| Compound 2 | 0.15 | 100 | — |
| Compound 3 | 23 | Not detected | Very weak |
| Compound 4 | 30 | Not detected | $1.1 \times 10^{-6}$ |
| Compound 5 | 48 | Not detected | $2.2 \times 10^{-6}$ |
| Compound 10 | 62 | Not detected | $4.4 \times 10^{-6}$ |

*NA: neuraminidase; The NAs used in this assay were derived from Arthrobacter Ureafaciens, *Clostridium perfringens*, *Vibrio cholerae*, and Influenza virus A/PR/8/34 (H1N1) and A/Aichi/2/68 (H3N2).
**: Km = $2.3 \times 10^{-4}$ M as for compound 1.

From the results shown in Table 1, p-nitrophenyl-α-O-glycoside derived of natural sialic acid (Compound 2) was completely hydrolyzed within 30 minutes, whilst p-nitrophenyl-α-O-glycosides of sialic acids modified in the 3-position (Compounds 3 to 5) were not hydrolyzed under the same conditions for 24 hours.

The sialidase inhibition test using capillary electrophoresis revealed that p-nitrophenyl-α-O-glycosides of sialic acids introduced with a hydroxyl group or fluorine atom in the 3-axial configuration (Compounds 4, 5 and 10) had potent inhibitory activities of Ki=about $10^{-6}$M to Clostridium perfringens sialidase.

Test Example 2

Inhibitory Activities of C-3 Modified Sialyl DSPE Derivatives Against Sialidases From Human Influenza A Viruses To examine whether Compounds 7 to 9 are inhibitory against sialidases, enzyme hydrolysis of compound 2 as a sialidase substrate was carried out. After incubation of the virus (A/PR/8/34 (H1N1) or A /Aichi/2/68) strains, 5 μg/ μl) with each derivative at a concentration of 250 μM at 37° C. for 1 h, it was found that the virus sialidase activity of was completely inhibited by Compound 9, but not by other derivatives examined. The $IC_{50}$ values of compound 4 against A/PR/8/34 (H1N1) and A/Aichi/2/68 (H3N2) were 62.50 and 31.25 μM, respectively Test Example 3

Inhibitory Activities of Ncu5Ac3 αF-DSPE Against the Sialidases From Influenza A Viruses of Different Host To examine the effect of Compound 9 against various influenza A virus sialidases, 16 strains of influenza virus isolated from humans, ducks and swine, were tested. As the result, it was shown that broad inhibitory spectrum of compound 9 against sialidases of all influenza viruses tested (Table 3). The $IC_{50}$ values of compound 9 for these viral sialidases varied from 15.6 to 500 μM with 4-MU-NeuAc as the substrate, and from 31.3 to 250 μM with compound 2 as the substrate.

Test Example 4

Inhibitory Activity Against Hemagglutinin Action

The influenza virus A/PR/8/34 (H1N1) and A/Aichi/2/68 (H3N2) strains were cultured using eggs of 15 days old at 35° C. for 48 hours, and purified by sucrose density gradient centrifugation.

Rabbit anti-influenza virus antibody was prepared by using the influenza virus A/PR/8/34 (H1N1) and A/Aichi/2/68 (H3N2) strains cultured in eggs as described above.

The test compounds (Compounds 6 to 9) were spotted on a TLC plate (Polygram Sil G; Macherey-Nagel, Germany).

The plate was developed with chloroform/methanol/12mM MgCl$_2$ (5:4:1, v/v/v) and blocked with 1% egg albumin (crystals; Taiyo Kagaku Company, Ltd., Japan) and 1% polyvinylpyrrolidone containing PBS solution (solution A) at room temperature for 2 hours. After the blocking solution was removed by suction, the plate was washed with PBS 3 times and incubated with a PBS suspension containing the A/PR/8/34 (H1N1) and A/Aichi/2/68 (H3N2) viruses in the 2$^8$ HA unit concentration (titer; for reference, Suzuki, Y . et al, Virology, 1992, 189, 121–131) at 4° C. for a maximum of 12 hours. The TLC plate was waashed with PBS 5 times, blocked with solution A at 4° C. for 30 minutes, further washed with PBS 3 times, and incubated with the aforementioned antibody solution at 4° C. for 2 hours. As the antibody, anti-influenza antibody diluted with 3% polyvinylpyrrolidone containing PBS solution (Solution B) to 1:1,000 was used. The plate was washed with PBS and blocked with solution A at 4° C. for 30 minutes. After the blocking solution was removed, the plate was further washed with PBS and incubated with horseradish peroxidase binding protein A (Organon Teknika N.V. Cappel Products) diluted with Solution B to 1:1,000 at 4° C. for 2 hours. Then, the plate was washed with PBS and incubated with a substrate solution (10 mM Tris-HCl buffer (pH 7.2), 0.3% 4-chloronaphthol, 3% H$_2$O$_2$ (5:1:0.02, v/v/v) at room temperature for 20 minutes. The virus binding activity of each compound was obtained by colorimetry using a double wavelength chromatoscanner (CR-910, Shimadzu, Kyoto) at the coloring of 620 nm (the control of 430 nm). The results are shown in Table 2 below.

In addition, virus hemagglutination inhibitory activity was determined as follows.

Determination of hemagglutination inhibitory activity was performed by using a 96-well microplate, a 0.01% (w/v) gelatin-PBS solution (pH 6.5) as a diluting buffer, and human erythrocytes. Virus suspension was added to a 0.01% (w/v) gelatin-PBS solution of each test compound (Compounds 6 to 9, initial concentration of 2 mM and then subjected to two-fold dilution), and the mixture was incubated at 4° C for 1 hour. Then, the mixture was added dropwise with 0.5% human erythrocyte-PSB suspension (0.5 mL/well) and then incubated at 4° C. for additional 1 hour. Inhibitory activities on the hemagglutination are shown as the lowest diluted concentration of the compound that completely inhibited agglutination. The results are shown in Table 2 below.

TABLE 2

Binding and inhibitory activity of Compounds 6 to 9 to influenza viruses A/PR/8/34 (H1N1) and A/Aichi/2/68 (H3N2)

| Compound | Substituent in the 3-position | Binding assay (%)* | | HAI (M)** | |
|---|---|---|---|---|---|
| | | H1N1 | H3N2 | H1N1 | H3N2 |
| Compound 6 | no substituent | N.D.*** | 25 | 1 × 10$^{-3}$ | 6.3 × 10$^{-5}$ |
| Compound 7 | OH (equatorial) | N.D. | 36 | 1 × 10$^{-3}$ | 3.1 × 10$^{-5}$ |
| Compound 8 | OH (axial) | N.D. | 32 | >1 × 10$^{-3}$ | 6.3 × 10$^{-5}$ |
| Compound 9 | F (axial) | N.D. | 33 | 1 × 10$^{-3}$ | 3.1 × 10$^{-5}$ |

*Binding activity of Compounds 6 to 9 to influenza viruses A/PR/8/34 (H1N1) and A/Aichi/2/68 (H3N2) (Binding activity of IV$^3$Neu5AcnLac4Cer was determined as the control, and used for comparison.)
**The hemagglutination inhibitory assay was carried out by using viruses (2$^4$ HA units) and each test compound at 4° C. for 1 hour.
***not detected From the result shown in Table 2, Compounds 7 to 9 substituted in the 3-position have affinity to H3 type virus HA to the same extent as that of Compound 6 having no substituent in the 3-position, and Compound 7 having a substituent in equatorial configuration in the 3-position have increased affinity of 144%. These compounds have no affinity to H1 type virus HA.

In addition, from the result shown in Table 2, HA inhibitory activity test revealed that Compounds 6 to 9 have potent inhibitory activities against H3 type virus HA (the HAI values of $\mu$M order).

Test Example 5

Inhibition of Infection of Influenza Virus to MDCK Cells

Ncu5Ac3 αF-DSPE inhibited the cell infection by influenza virus in the early and late stages To confirm the effects of synthetic sialyl DSPE derivatives on influenza virus infection, neutralization of influenza virus A/Aichi/2/68 (H3N2) strain by the derivatives was examined as their cytopathic effects on MDCK cells. The activities of lactate dehydrogenase (LDH) released from the infected cells was measured to estimate influenza virus. Synthetic sialyl DSPE derivatives inhibited the infection of A/Aichi/2/68 (H3N2) virus to MDCK cells in a dose dependent manner (IC$_{50}$, 5 $\mu$M to 70 $\mu$M). Neu5Ac3 a F-DSPE markedly inhibited the infection of A/Aichi/2/68 (H3N2) in comparison with those of other sialyl DSPE derivatives examined. The IC$_{50}$ of Compound 9 against A/Aichi/2/68 (H3N2) was 5,6 $\mu$M, 8-fold stronger than those of Compounds 6 to 8.

To investigate the inhibitory mechanism of the derivatives, the process of virus infection was divided into pro- and post-stages. After incubation of the virus with the derivatives for 2 h, the mixture was added to the culture medium of MDCK cells and maintained for 1 h. The inhibitory activities of the derivatives were measured after removal of the mixture, washing and maintaining the cells in serum-free MEME for 20 h. The inhibitory of Compound 9 was significantly decreased (IC$_{50}$=14 $\mu$M), whereas those of the other derivatives showed similar inhibitory activities (IC$_{50}$=ca. 50 $\mu$M). On the other hand, in order to see the inhibitory activities of the derivatives against the released new-viruses, the LDH activities from infected cells were determined adding the derivatives to the infected-cells and incubation for 20 h. The experimental data showed that only Compound 9 prevented the cytopathic effects with IC$_{50}$ value of ca. 40 $\mu$M, but not other derivatives examined. The results indicated that Compound 9 acted on not only the early stage where virus infect by attachment of hemagglutinin with its ligands but also late stage of the replication of influenza virus, whereas the other derivatives only inhibited the adhesion of virus to cellular membrane. Accordingly, the stronger inhibitory effect observed in the first experiment is considered due to synergistic effect of inhibition of both processes.

TABLE 3

Inhibitory activity of Neu5Ac3αF-DSPE against the sialidase activities of various influenza A viruses.

| | Inhibitory activity (IC$_{50}$, $\mu$M) | |
|---|---|---|
| Influenza viruses | 4-MU-Neu5Ac as substrate | Neu5Ac-DSPE as substrate |
| Human isolates | | |
| A/PR/8/34 (H1N1) | 62.5 | 31.3 |
| A/Singapore/1/57 (H2N2) | 15.6 | 62.5 |
| A/Aichi/2/68 (H3N2) | 31.3 | 31.3 |

TABLE 3-continued

Inhibitory activity of Neu5Ac3αF-DSPE against the sialidase activities of various influenza A viruses.

| | Inhibitory activity (IC$_{50}$, μM) | |
|---|---|---|
| Influenza viruses | 4-MU-Neu5Ac as substrate | Neu5Ac-DSPE as substrate |
| Avian isolates | | |
| A/duck/36/4/76 (H1N1) | 125 | 62.5 |
| A/duck/849/3/80 (H4N1) | 125 | 125 |
| A/duck/13/2/76 (H6N1) | 150 | 180 |
| A/duck/33/3/76 (H10N1) | 500 | 250 |
| A/duck/273/8/78 (H2N2) | 150 | 125 |
| A/duck/24/5/76 (H3N2) | 180 | 100 |
| A/duck/47/5/76 (H7N2) | 200 | 150 |
| A/duck/86/1/76 (H9N2) | 180 | 125 |
| A/duck/313/4/78 (H5N3) | 62.5 | 62.5 |
| A/duck/44/3/76 (H11N3) | 250 | 75 |
| A/duck/862/5/80 (H12N5) | 125 | 100 |
| Swine isolates | | |
| A/swine/Hokkaido/2/81 (H1N1) | 62.5 | 125 |
| A/swine/Italy/309/83 (H3N2) | 125 | 150 |

According to the present invention, novel medicaments are provided which have inhibitory activities against both hemagglutinin and sialidase which are mrnembrane binding proteins of influenza virus. The medicaments of the present invention are useful for preventive and/or therapeutic treatment of viral infectious diseases such as influenza virus infections.

What is claimed is:

1. A medicament which comprises as an active ingredient a compound represented by the following formula:

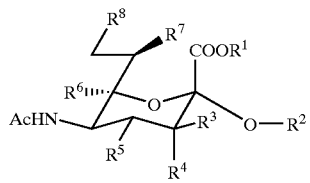

wherein $R^1$ represents a hydrogen atom or an optionally substituted $C_{1-6}$ alkyl group; $R^2$ represents an optionally substituted phenyl group, an optionally substituted $C_{1-20}$ alkyl group, an optionally substituted $C_{1-20}$ alkenyl group, or —(CH$_2$)$_k$—[NH—(CH$_2$)$_m$—NH]$_n$—Y or —(CH$_2$)$_k$—[NH—(CH$_2$CH$_2$O)$_{m-1}$—CH$_2$CH$_2$NH]$_n$—Y in which Y represents a phosphatidylethanolamine residue or a polyglutamic acid residue, k and m independently represent an integer of from 2 to 10, n represents 0 or 1, provided that when n represents 1, Y represents a phosphatidylethanolamine residue; one of $R^3$ and $R^4$ is a hydrogen atom and the other one of $R^3$ and $R^4$ is a halogen atom or an optionally substituted hydroxyl group; and $R^5$, $R^6$, $R^7$ and $R^8$ independently represent an optionally substituted hydroxyl group; or a pharmaceutically acceptable salt, hydrate or solvate thereof.

2. The medicament of claim 1, wherein $R^3$ is a hydrogen atom, and $R^4$ represents a halogen atom or an optionally substituted hydroxyl group.

3. A medicament which comprises as an active ingredient a compound represented by the following formula:

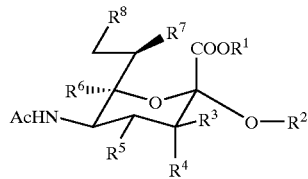

wherein $R^1$ represents a hydrogen atom; $R^2$ represents a distearoyl phosphatidylethanolamine residue; $R^3$ and $R^4$ both are a hydrogen atom; and $R^5$, $R^6$, $R^7$ and $R^8$ are hydroxyl groups; or a pharmaceutically acceptable salt, hydrate or solvate thereof.

4. A method of preventing a viral infectious disease in a subject, wherein the method comprises administering to the subject an effective quantity of the medicament of claim 1.

5. A method of preventing a viral infectious disease in a subject, wherein the method comprises administering to the subject an effective quantity of the medicament of claim 2.

6. A method of preventing a viral infectious disease in a subject, wherein the method comprises administering to the subject an effective quantity of the medicament of claim 3.

7. A method of treating a viral infectious disease, wherein the method comprises administering an effective quantity of the medicament of claim 1 to a subject in need thereof.

8. A method of treating a viral infectious disease, wherein the method comprises administering an effective quantity of the medicament of claim 2 to a subject in need thereof.

9. A method of treating a viral infectious disease, wherein the method comprises administering an effective quantity of the medicament of claim 3 to a subject in need thereof.

10. The method of claim 4, wherein the viral infectious disease comprises an influenza virus infectious disease.

11. The method of claim 5, wherein the viral infectious disease comprises an influenza virus infectious disease.

12. The method of claim 6, wherein the viral infectious disease comprises an influenza virus infectious disease.

13. The method of claim 7, wherein the viral infectious disease comprises an influenza virus infectious disease.

14. The method of claim 8, wherein the viral infectious disease comprises an influenza virus infectious disease.

15. The method of claim 9, wherein the viral infectious disease comprises an influenza virus infectious disease.

16. A method of inhibiting at least one of the infectious activity and the proliferation of influenza virus, wherein the method comprises administering an effective quantity of the medicament of claim 1 to a subject in need thereof.

17. A method of inhibiting at least one of the infectious activity and the proliferation of influenza virus, wherein the method comprises administering an effective quantity of the medicament of claim 2 to a subject in need thereof.

18. A method of inhabiting at least one of the infectious activity and the proliferation of influenza virus, wherein the method comprises administering an effective quantity of the medicament of claim 3 to a subject in need thereof.

* * * * *